United States Patent [19]

Wild

[11] Patent Number: 5,176,636
[45] Date of Patent: Jan. 5, 1993

[54] DEVICE FOR INTUBATION OF HUMAN PASSAGES FOR DIAGNOSTIC AND THERAPEUTIC PURPOSES

[76] Inventor: John J. Wild, 4262 Alabama Ave. S., Minneapolis, Minn. 55416

[21] Appl. No.: 732,139

[22] Filed: Jul. 18, 1991

[51] Int. Cl.5 .............................................. A61M 29/00
[52] U.S. Cl. .......................................... 604/96; 604/99
[58] Field of Search ................................. 604/96-104, 604/247, 256; 606/192-199

[56] References Cited

U.S. PATENT DOCUMENTS

| | | | |
|---|---|---|---|
| 3,707,151 | 12/1972 | Jackson | 604/96 |
| 4,813,935 | 3/1989 | Haber et al. | 604/99 |
| 5,085,636 | 2/1992 | Burns | 604/99 |

*Primary Examiner*—John D. Yasko
*Attorney, Agent, or Firm*—J. R. Cwayna

[57] ABSTRACT

A device for rapid intubation of devices into internal human passages for both diagnostic and therapeutic purposes. The device includes a conduit surrounded by a thin walled, inflatable and longitudinally and radially expandable member which will initially drive the device into the selected passages such as the lower bowel, colon, esophagus or upper bowel. Controlled inflation of such member provides the driving, positioning force for proper intubation even through particularly difficult transition portions of the selected passage. Partial or total deflation of the expandable member allows sealing for therapeutic utilization, evacuation of the passage for passage inspection or combinations of such useages. The device is easily adapted to accomodate diagnostic or treatment devices while allowing cooperative control thereof exteriorally of the body.

10 Claims, 2 Drawing Sheets

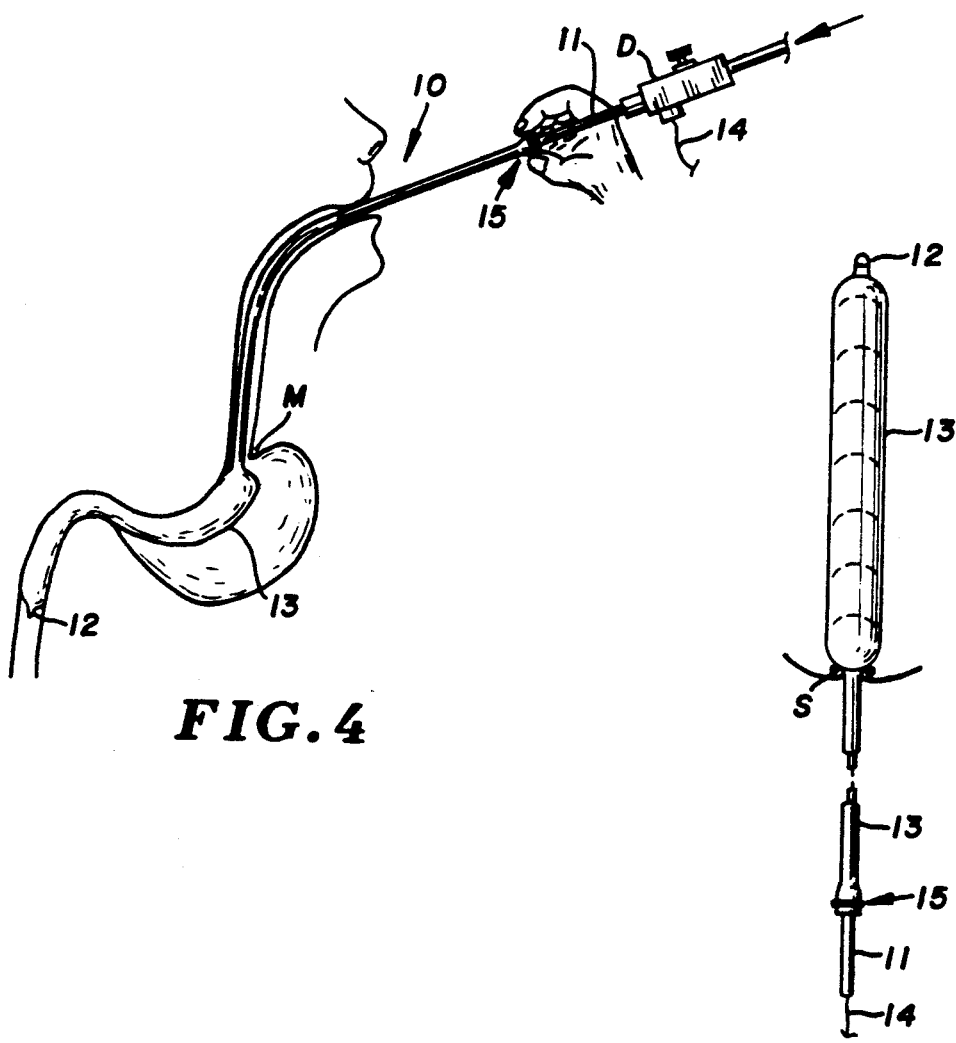
FIG.4
FIG.5
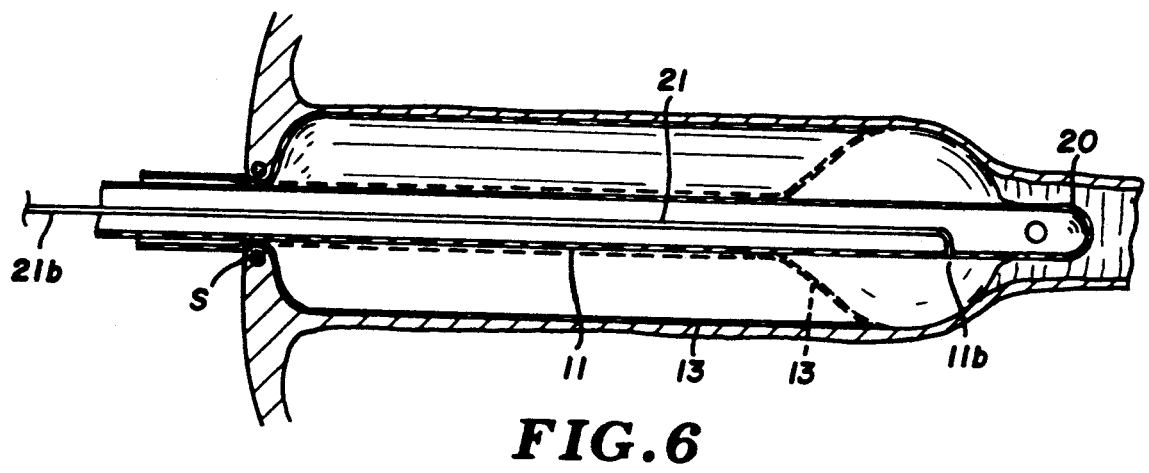
FIG.6

DEVICE FOR INTUBATION OF HUMAN PASSAGES FOR DIAGNOSTIC AND THERAPEUTIC PURPOSES

RELATED APPLICATIONS

There are no related applications on file in the U.S. Patent Office which should be considered inconnection with this application.

FEDERAL SPONSORSHIP

This invention has not been made under any federally sponsored research and development arrangement nor under any other sponsored research and development program.

FIELD OF THE INVENTION

This invention relates to a device for rapid intubation of devices for either diagnostic or therapeutic purposes into human passages and more particularly to a device which will rapidly and safely advance the diagnostic or treatment device to a desired area of an internal passage for treatment or examination.

SUMMARY OF THE INVENTION

A device provided for rapid and safe intubation of either diagnostic or therapeutic appliances into internal human passages which relies to a certain extent upon a body portion for attaining advancement force into areas such as the upper and lower bowel.

The device basically includes a flexible, hollow conduit arranged with an operative or an examination head arranged on one end thereof. For operative or therapeutic purposes the head may be used to introduce medicants or substances such as radio opaque materials or, conversely, may be used to remove material from the passage. In the case of the diagnostic mode a diagnostic head is provided and a conductor is carried internally of the conduit.

An inflation conduit is carried interiorly of the conduit for ordinary inflation of the flexible member to provide for travel of the device into the passage and for selective inflation of the flexible member when, the flexible member will perform as a seal within the passage for introduction of medicants to an isolated area or to assist in evacuation of a specific passage area.

A manual slip valve is provided between the inflatable member and the conduit at the accessible end of the conduit to assist in controlled deflation and inflation of the flexible member. This manual valve includes a pressure held valve which releases internal pressure upon longitudinal movement of the same upon the internal conduit.

The thin walled, flexible, distensible member provides for longitudinal expansion and therefore longitudinal introduction into the passage and particularly across difficult anatomic transition areas such as the stomach when intubating the upper bowel.

The thin walled, flexible, distensible member also provides for selective inflation at, particularly, the innermost or operative end of the conduit.

Examination functions can be performed in static or dynamic conditions with information from the sensor carried by the internal conductors of the conduit while therapeutic operations will best be carried on with the unit in a static position.

PRIOR ART AND BACKGROUND OF THE INVENTION

In a consideration of the prior art of which he is well aware, a search of the Patent Office records resulted in finding Pat. Nos. to Farahany, No. 4,850,3349; Bronson, No. 4,327,720; Powell, No. 4,638,805; Lee, No. 2,813,531; Rosenberg, No. 4,645,490 and Chin, No. 4,696,304. More applicable art, though older than the art resulting from such Patent Office search, lies in two articles authored by the inventor hereof. These are: "The Stomach as a Cause of Difficulty in Intubating the Human Duodenum", *SURGERY, St. Louis*, vol. 24, No. 1, Pages 70–78, July 1948; and "Further Development of the Gastric Balloon to Facilitate Intestinal Intubation", *SURGERY, St. Louis*, vol 27, No. 2, Pages 245–253, Feb. 1950.

Neither the cited prior patent art nor do the articles by the inventor provide for the rapid and safe intubation of commonly useable diagnostic or therapeutic appliances which are positionable into the upper or lower bowel sections through either the anus or mouth and particularly through the stomach after introduction into the mouth.

Cancer of the bowel has a particular propensity for stealth in that by the time it manifests its presence by symptoms, it has reached a stage where removal does not guarantee a cure because of the possibility of having already spread to remote sites of the body. Detection at earliest stages is vital to a successful cure. For this reason the earliest asymptomatic stages must be detected in a symptom free population and thus a large number of persons must be examined. Examination must be rapid and thorough and therefore the inventor provides a system which, in one form, provides for intubation of suitable diagnostic appliances and which, in another form, provides for intubation of therapeutic devices.

To date, medical practice for detection of lower bowel abnormalities is carried out by injection of a radio-opaque solution through a catheter inserted in the anus to initially fill the bowel with examination carried out by X-ray imaging of the area with subjective interpretation by a skilled radiologist. Applicant's device allows for selective placement of the barium and a simple method of such placement. A more labor intensive and exact examination is made by sigmoidoscopy which, in the present state of the art, is carried out through use of a long, flexible and controllable optical sigmoidoscope. The instrument is passed through the anus and, under directed visual observation, using air injection and hand manipulation, advanced along the bowel so only the surface of the bowel can be directly, visually inspected by a skilled operator.

Neither of these methods provides rapid interrogation for presence of an abnormality beneath the surface of the passage.

Present devices for intubation, to the knowledge of the applicant, do not consider medicant placement nor do they consider selective evacuation.

It is a prime purpose of the applicant's invention to provide a means for rapidly and safely introducing an abnormality sensing device into internal human passages which will allow histological examination thereof in a rapid manner and which will not endanger nor damage the inner surface of the passage through such introduction.

It is a further object of the applicant's invention to provide a device for introduction of a histological abnormality sensing device into internal human passages such as the upper and lower bowel sections for systematic examination of the same upon insertion or withdrawal of the device.

It is still a further object of the applicant's invention to provide a device for examination of internal human passages which maintains an exposed sensing or examination head in a position within the passage to normally prevent contact with the inner surface thereof to prevent damage thereto It is still a further object of the applicant's invention to provide a device which may be used in examination of either the upper or lowel bowel which is equally easily insertable through the mouth and through the stomach or through the anus.

It is a further object of the applicant's invention to provide a device for the rapid intubation of an operative appliance into human passages for medicant administration interiorally of the passage.

It is yet a further object of the applicant's invention to provide a device for rapid intubation of an operative appliance into human passages which may be utilized to act directly on the contents of the passage such as evacuation thereof.

These and other objects and advantages of the applicant's invention will more fully appear from a consideration of the accompanying drawings and description.

DESCRIPTION OF THE DRAWINGS

FIG. 4 is an illustration of the device of applicant's invention as the same would be inserted through the mouth, esophagus, across the stomach and into the upper bowel acting against the cardiac esophagial sphincter;

FIG. 5 is a view similar to FIG. 3 illustrating the device arranged for therapeutic utilization and illustrating, through a dotted line arrangement, selective inflation of the flexible, pneumatic member included with the device; and, FIG. 6 is a schematic illustration of the device as the same is inflated for resultant introduction into the bowel through the anus and acting against the anal sphincter muscle.

DESCRIPTION OF A PREFERRED FORM OF THE INVENTION

Figure 1:
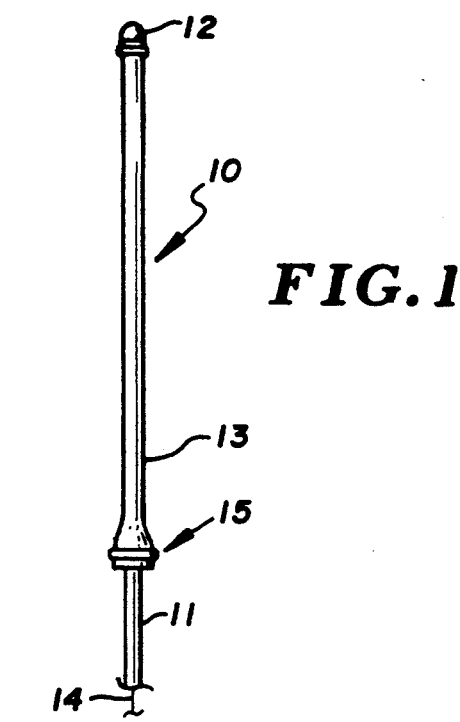
FIG. 1 is a simple, longitudinal elevation of the device embodying the concepts of the invention.
Figure 2:
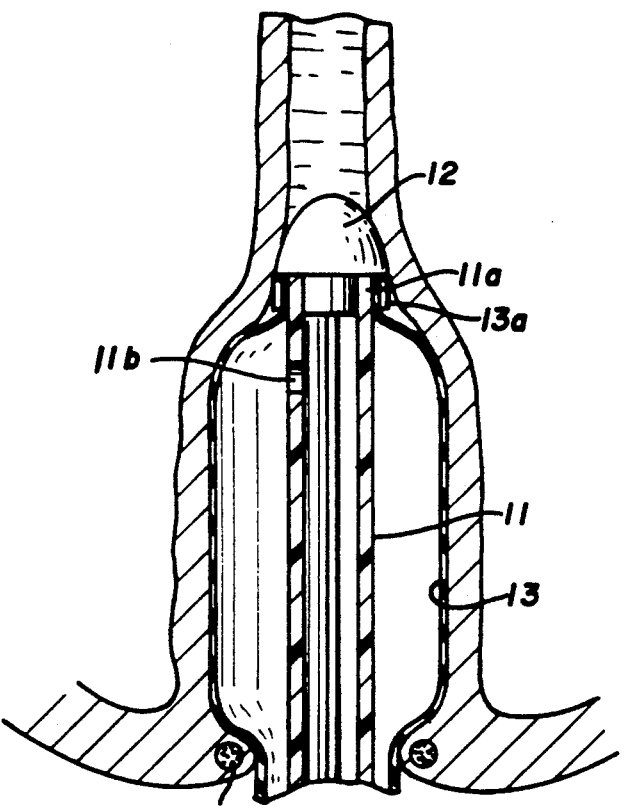
FIG. 2 is an illustration of a first form of the device embodying the concepts of the applicant's invention as the same would be inserted through the anus into the lower bowel for examination thereof.
Figure 2:
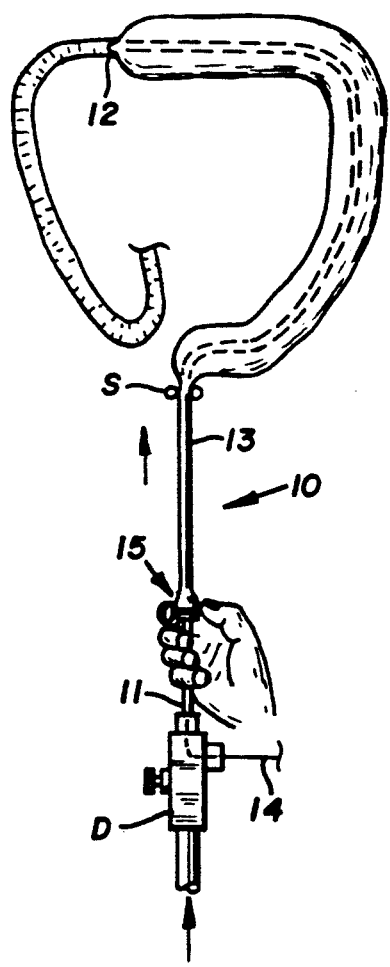

In accordance with the accompanying drawings, the intubation device, when the same is utilized as an examination head appliance placement device is designated in its entirety 10 and includes as its essential elements, a longitudinally extending, generally flexible, hollow conduit 11; a sensing head 12 selected in accordance with the desired examination procedure; a flexible, fluid fillable distensible member 13 extending substantially the entire length of conduit 11 and an information conductor 14 arranged within conduit 11. As illustrated, the sensing head 12 and one end of the flexible, inflatable member 13 are secured to and sealed to one end 11a of conduit 11 through a common clamp member 13a. At least one filling aperture 11b allows communication from the hollow interior of conduit 11 to the interior of such flexible member 13 for filling or pressurizing thereof with such pressurizing or filling resulting in movement of the device 10 into the selected passage. A filling device D is illustrated at the ultimate end 11c of conduit 11. Obviously means must be made for extraction of conductor 14 at such end 11c of conduit 11 for relay of information to a diagnostic apparatus in accordance with the examination technique selected.

What may be termed a rolling valve 15 is provided at the ultimate end 13b of the flexible, expandable envelope 13. The uniqueness of this valve 15 lies in its two position arrangement to seal in a first, as illustrated, solid line position and to permit deflation and collapse of member 13 in a second, dotted line position.

As illustrated, a pair of ring clamps 16a, 16b are provided in a manner to bound a folded ply section of material of envelope 13 with the inner clamp 16b being greater in diameter than the conduit 11 to permit a single layer of envelope material to be folded thereagainst upon movement of the conduit 11 relative to the envelope 13 in one direct and to lie against the conduit 11 in sealing position when the conduit 11 is moved in the opposite direction. Numeral 17 is again used for the solid line, sealing position. In this solid line position, positive pressure exists within envelope 13 and movement of the conduit 11 is in the direction of the ply layer. This sealing position permits movement of the conduit 11 relative to the envelope 13 and particularly in the condition of longitudinal expansion of the envelope 13 and thus advancement of the conduit 11 and sensing head 12 into the desired area of examination. In the dotted line position, evacuation of the enveloping membrane is permitted and withdrawal examination of the head 12 and the envelope 13 is permitted.

This valve 15 then functions to allow advancement of both the envelope 13 and contained conduit 11 as the unit envelope 13 is being inflated. Rollover of the valve 15 allows deflation and thus withdrawal of both the envelope 13, conduit 11 and examining head 12.

Advancement of the unit through the mouth, esophagus and stomach is illustrated in FIG. 4. As illustrated, the article is hand held and initially hand fed through the stomach until located at the bowel entrance. Inflation, at this time, causes inflation of the forward portion of the envelope 13 and this enlargement will abut with the lower end of the esophagus at the cardiac esophagial sphincter muscle M. Further inflation causes the envelope to enlarge longitudinally from this abutment point to push the sensor and accompanying envelope 13 into the upper bowel.

Figure 3:
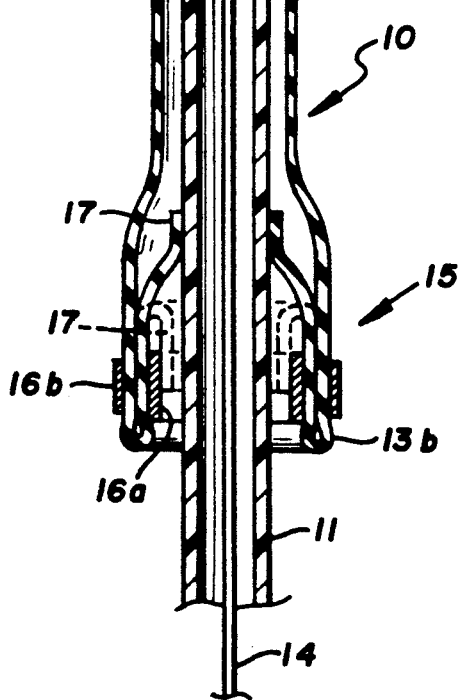
FIG. 3 is a longitudinal section of the device as illustrated in FIG. 1, at an enlarged scale, particularly illustrating in dotted position the manual shifting of the inflation release valve and the pressurized sealing obtained therefrom in solid line position.

Advancement and lower bowel placement is best illustrated in FIG. 3. Initial placement is made through the anus and the anal sphincter muscle S acts as the abutment for advancement thereafter with inflation distending the flexible envelope 13 longitudinally to force the sensor 12 into the bowel. Release or roll of valve 15 allows deflation and withdrawal of the unit with examination taking place during withdrawal.

It should be obvious to one skilled in the art that interrogation of tissue may be made during introduction or withdrawal of the device.

The form of the invention that is directly related to a therapeutic utilization is illustrated in the longitudinal cross section of FIG. 5. As illustrated therein, anal introduction is attained and certain previously illustrated and identical elements are utilized with the same reference numerals used therefore. In this instance the head 20 is provided with a contoured outer shape to facilitate travel through the passage and is provided with passages 20a therethrough for introduction or removal of material from the passage. Transmission of such material is through conduit 11. In this instance, a separate inflation tube 21 is utilized with communication to the interior of the flexible envelope 13 being through opening 11b of conduit 11. The accessible end 21b provides inflation control to the forward end of envelope 13 with valve 15 again being used for deflation, whether such deflation be partial or full deflation.

The dotted line formation of the forward end of the flexible envelope illustrates a method of partial inflation to provide an internal seal for localized introduction of materials such as medicants to isolated areas of the passage. Similarly evacuation of the passage is afforded through passages 20a of the head 20. This selected inflation is well known in balloon art. After distention through inflation, this forward area of the member 13 is more easily distended than areas therebehind and introduction of air, after deflation will result in the arcuate expansion as illustrated in FIG. 5. In this manner, an isolation seal is provided for the intended useage.

In either situation, lubrication of the device may be provided with a radio-opaque substance to provide lubrication and to provide detection of any leakages through the passage wall by subsequent X-ray examination.

It should be obvious that the applicant has provided a new and unique passage intrusive device which will provide for rapid placement of a diagnostic or therapeutic appliance into internal human passages.

What is claimed is:

1. A device for rapid intubation of human passages for diagnostic and therapeutic purposes including:
   a. a longitudinally extending hollow flexible conduit having a first and a second end;
   b. a pneumatic distendable and extensible envelope surrounding said conduit and being sealingly attached thereto at a first end thereof and having a second end;
   c. an appliance head arranged on said first end of said conduit for transport therewith;
   d. means for releasably sealing the second end of said envelope to said conduit at a position exteriorly of the passage for control thereof; and,
   e. means for introducing an expansion pressure to said envelope adjacent said first end thereof interiorly of the passage.

2. The device as set forth in claim 1 wherein said means for releasably sealing said second end of said envelope includes valving means providing clamp means engaging selected portions of said envelope end providing a pressure sealing flap sealingly engageable with said conduit in said first position and disengaged from sealing position with said conduit in a second position.

3. The device as set forth in claim 2 wherein said clamp means are spaced from said end of said envelope to provide a pressure controlling sealing flap.

4. The device as set forth in claim 3 and the inner circumference of said clamp allowing said flap to be shiftable between said clamp and said conduit in said second position and releasing pressure from said envelope in said second position.

5. The device as set forth in claim 1 and said envelope being distendable and extensible in a ratio to provide a longitudinally increasing member upon pressurization for movement of said conduit and head through a human passage.

6. The device as set forth in claim 1 and said means for pressurizing said envelope including a tubular member within said conduit.

7. The device as set forth in claim 1 wherein envelope is selectively expandable adjacent said first end thereof to permit positioned expansion within the passage to provide a seal therein.

8. The device as set forth in claim 1 wherein said appliance head includes a diagnostic examining head and means for providing energy to and receiving energy therefrom is provided through said conduit.

9. The device as set forth in claim 1 wherein said appliance head includes apertures therethrough for introduction of medicants therethrough into the passage.

10. The device as set forth in claim 1 wherein said appliance head includes apertures therethrough for evacuation of the passage.

* * * * *